(12) United States Patent
Treiber et al.

(10) Patent No.: US 7,093,492 B2
(45) Date of Patent: Aug. 22, 2006

(54) CONFIGURABLE VIBRATION SENSOR

(75) Inventors: Mark Treiber, Mississauga (CA); Christopher McClellan, Kitchener (CA); Farid Golnaraghi, Waterloo (CA)

(73) Assignee: Mechworks Systems Inc., Waterloo (CA)

( * ) Notice: Subject to any disclaimer, the term of this patent is extended or adjusted under 35 U.S.C. 154(b) by 3 days.

(21) Appl. No.: 10/804,047

(22) Filed: Mar. 19, 2004

(65) Prior Publication Data

US 2005/0204820 A1    Sep. 22, 2005

(51) Int. Cl.
*G01H 1/00* (2006.01)
(52) U.S. Cl. .......................... 73/659; 73/660
(58) Field of Classification Search ............... 73/660, 73/659
See application file for complete search history.

(56) References Cited

U.S. PATENT DOCUMENTS

| | | | | |
|---|---|---|---|---|
| 4,044,239 A | * | 8/1977 | Shimauchi et al. | 700/280 |
| 4,063,450 A | * | 12/1977 | Lyons | 73/579 |
| 4,215,404 A | * | 7/1980 | Bukhtiyarov et al. | 701/102 |
| 4,980,844 A | * | 12/1990 | Demjanenko et al. | 702/56 |
| 5,041,989 A | * | 8/1991 | Kataoka et al. | 702/39 |
| 5,309,149 A | | 5/1994 | Bozeman | |
| 5,758,311 A | * | 5/1998 | Tsuji et al. | 701/111 |
| 5,847,658 A | * | 12/1998 | Irie et al. | 340/683 |
| 5,955,669 A | * | 9/1999 | Egami | 73/579 |
| 6,032,109 A | | 2/2000 | Ritmiller | |
| 6,205,872 B1 | | 3/2001 | Pflueg | |
| 6,295,510 B1 | | 9/2001 | Discenzo | |
| 6,297,742 B1 | | 10/2001 | Canada et al. | |
| 6,601,005 B1 | | 7/2003 | Eryurek et al. | |

* cited by examiner

*Primary Examiner*—Hezron Williams
*Assistant Examiner*—Rose M. Miller
(74) *Attorney, Agent, or Firm*—Bereskin & Parr

(57) ABSTRACT

A configurable vibration sensor having a sensor circuit, an analog-to-digital converter and a processor is provided. The sensor circuit employs a vibration sensing element and a variable bandwidth filter controllable by the processor. In addition to the variable bandwidth filter, other configurable elements may also be employed in the sensor circuit, including a variable gain amplifier. These configurable elements allow the configurable vibration sensor to be configured for different vibration measurement applications when measuring vibrations from vibrating structures such as machinery and the like.

40 Claims, 5 Drawing Sheets

CONFIGURABLE VIBRATION SENSOR

FIELD OF THE INVENTION

Embodiments of the invention relate generally to vibration sensors for use with vibrating structures such as machinery and the like, and more specifically to vibration sensors that can be configured for different vibration measurement applications.

BACKGROUND OF THE INVENTION

Machines and other vibrating structures generate characteristic vibrations during their normal operations. These vibrations can vary from a simple sinusoidal type, to a complex, multi-frequency, non-linear oscillation or random type. Changes in the oscillation form of vibrations emanating from such machinery can result from a simple change in operation, but they may also be the result of wear, failure or fatigue of mechanical parts. By analyzing and isolating the characteristics of the vibrations of a machine, early warning signs of machine failures can be detected. This information may be used to prevent unscheduled downtime of the machine, thereby increasing machine efficiency.

Vibrations are typically measured using analog vibration sensing elements, such as analog accelerometers, positioned on machinery at strategic locations. The vibration sensing elements are selected so that the observed amplitude and frequency range optimally measure the vibrations at a specific location. Separate analog filters, such as band-pass and low-pass filters, may be attached to the analog output of a vibration sensing element to further adjust the vibration signal measured by the vibration sensing element. The result is that a cornucopia of vibration sensing elements and filters may be distributed on a single machine.

The output of a vibration sensing element may also be subject to further analysis. Typical calculations can include the Root-Mean-Square Average (RMS), peak-to-peak amplitude, as well as a Fast Fourier Transform of the vibration signal, to determine the dominant frequencies in the signal. In simple vibration sensors containing a vibration sensing element, these calculations are typically accomplished in embedded hardware.

Where more complex analysis is desired, vibration signals are often digitized. The analog signals output from vibration sensing elements spread across a machine may be wired to a single point for analog-to-digital conversion. From these digital signals, not only may the above-mentioned typical calculations be performed, but also more sophisticated calculations such as modal analysis, correlations, and other computationally intensive functions may be performed.

A number of vibration sensors and vibration monitoring devices exist in the prior art. For example, in one prior art device, vibrations are measured at a single point on a machine using a vibration data logger. The data logger is a self-contained unit that includes a vibration sensing element together with an analog-to-digital converter and random access memory (RAM). This device is secured to the machine, and stores a record of the vibrations measured over a period of time. The device may be subsequently detached from the machine in order to download stored vibration data to a personal computer for analysis.

Further examples of other prior art vibration sensors or vibration monitoring devices are described in the following references: U.S. Pat. No. 5,309,149; U.S. Pat. No. 5,847,658; U.S. Pat. No. 6,032,109; U.S. Pat. No. 6,205,872; U.S. Pat. No. 6,295,510; U.S. Pat. No. 6,297,742; and U.S. Pat. No. 6,601,005.

SUMMARY OF THE INVENTION

In one broad aspect of the invention, there is provided a configurable vibration sensor for sensing vibrations from vibrating machinery.

In another broad aspect of the invention, there is provided a single vibration sensor that can be configured for different vibration measurement applications, so that the functions of many different components that might typically be used to measure vibrations on a particular machine can be performed by a single sensor.

In another broad aspect of the invention, there is provided a configurable vibration sensor comprising: one or more sensor circuits; one or more analog-to-digital converters coupled to the one or more sensor circuits, for converting output from the one or more sensor circuits to one or more digital signals; and a processor coupled to the one or more analog-to-digital converters, for processing the one or more digital signals; wherein each of the one or more sensor circuits comprises a vibration sensing element and a variable bandwidth filter coupled thereto; and wherein each variable bandwidth filter of the one or more sensor circuits is controllable by the processor such that the operation of each variable bandwidth filter is variable by the processor.

In another broad aspect of the invention, there is provided a configurable vibration sensor comprising: one or more sensor circuits; one or more analog-to-digital converters coupled to the one or more sensor circuits, for converting output from the one or more sensor circuits to one or more digital signals; and a processor coupled to the one or more analog-to-digital converters, for processing the one or more digital signals; wherein each of the one or more sensor circuits comprises a vibration sensing element, a variable bandwidth filter, and a variable gain amplifier; wherein each variable bandwidth filter of the one or more sensor circuits is controllable by the processor such that the operation of each variable bandwidth filter is variable by the processor, and wherein each variable gain amplifier of the one or more sensor circuits is controllable by the processor such that the operation of each variable gain amplifier is variable by the processor.

In another broad aspect of the invention, there is provided a configurable vibration sensor adapted for coupling to an external device, such as a computer for example, through a communications interface.

In another broad aspect of the invention, there is provided a sensor circuit for a configurable vibration sensor, the sensor circuit for coupling to a processor through an analog-to-digital converter, the sensor circuit comprising: a vibration sensing element; and a variable bandwidth filter coupled to the vibration sensing element; wherein the variable bandwidth filter is controllable by the processor such that the operation of the variable bandwidth filter is variable by the processor.

In another broad aspect of the invention, there is provided a sensor circuit for a configurable vibration sensor, the sensor circuit for coupling to a processor through an analog-to-digital converter, the sensor circuit comprising: a vibration sensing element; a variable bandwidth filter coupled to the vibration sensing element; wherein the variable bandwidth filter is controllable by the processor such that the operation of the variable bandwidth filter is variable by the processor; and a variable gain amplifier coupled to the vibration sensing element, wherein the variable gain amplifier is controllable by the processor such that the operation of the variable gain amplifier is variable by the processor.

BRIEF DESCRIPTION OF THE DRAWINGS

These and other features of embodiments of the invention will be made apparent from the following description with reference to the accompanying drawings, in which.

DETAILED DESCRIPTION OF EMBODIMENTS OF THE INVENTION

Figure 1:
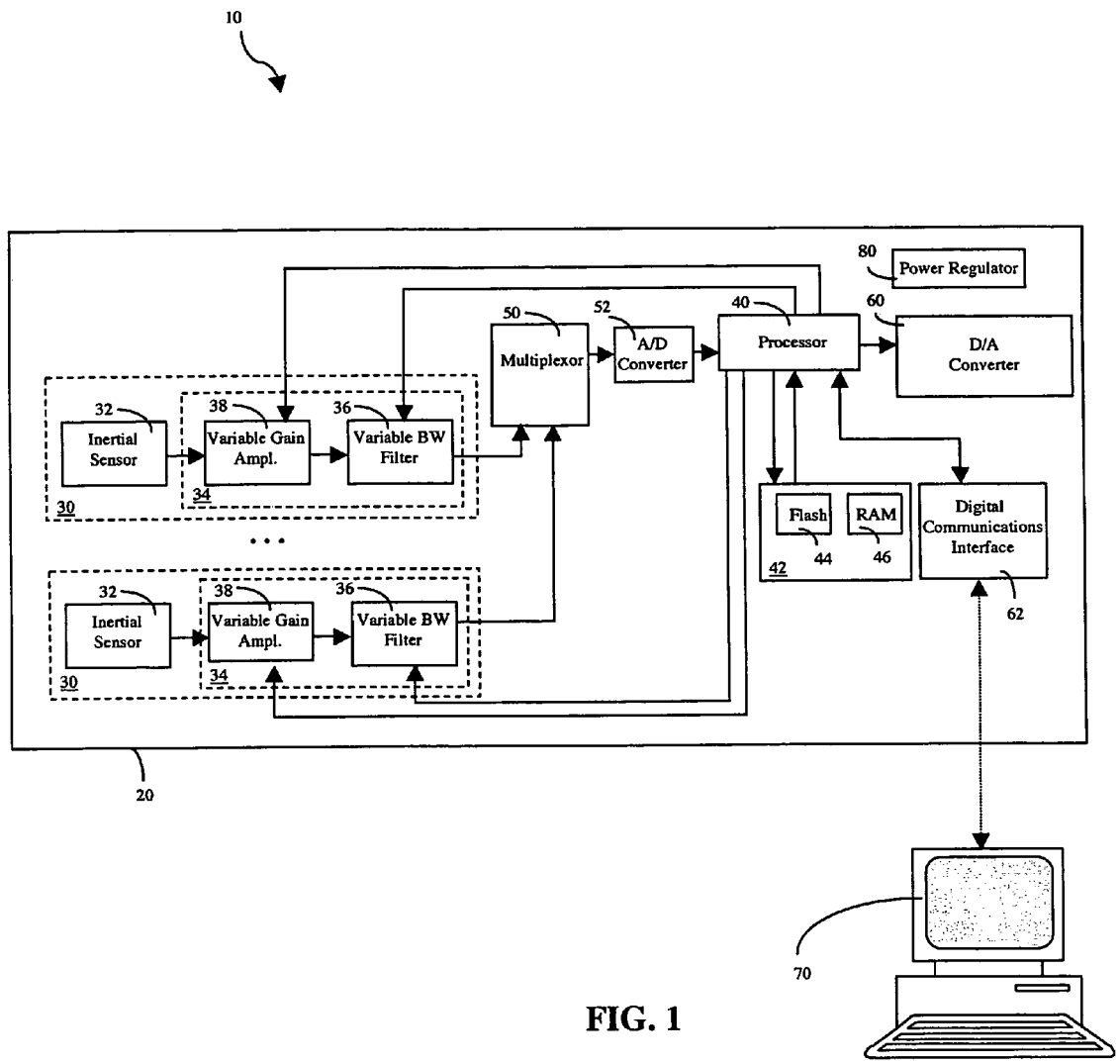
FIG. 1 is a schematic diagram of a configurable vibration sensor in an embodiment of the invention.

Embodiments of the invention are directed to vibration sensors for detecting vibrations in vibrating structures such as machinery and the like. These vibration sensors are referred to herein as configurable vibration sensors, as they can be configured for different vibration measurement applications. For example, an accelerometer attached to a bearing housing would require a large bandwidth to observe vibrations due to the bearing itself, while the same sensor could also be used to monitor oscillations or sway in a machine that includes the previously mentioned bearing housing using a much smaller bandwidth.

The term "configure" and derivations thereof as used in the specification and in the claims is not restricted to meaning that such action may only be performed once. For example, in some embodiments of the invention, the configuration of a vibration sensor may be set only once, while in other embodiments of the invention, the configuration of a vibration sensor may be changed once or multiple times. The meaning of the term "configure" and derivations thereof is intended to encompass such scenarios.

In one embodiment of the invention, the configurable vibration sensor comprises an enclosure adapted for mounting to the machinery that is to be observed. The enclosure is constructed so that the mechanical structure of the enclosure does not significantly modify the transmission of vibrations from the machinery to the vibration sensing element. This can include any techniques used to make the configurable vibration sensor, as a unit, more rigid. One or more analog vibration sensing elements, such as analog accelerometers, are situated within the enclosure. Each vibration sensing element generates an analog signal as output, which is then provided to a configurable analog signal conditioning circuit. The output of each configurable analog signal conditioning circuit is provided to an analog multiplexor, which provides a selected output to an analog-to-digital converter. The analog-to-digital converter provides a processor with output from one or more selected configurable analog signal conditioning circuits in digital form for further processing and analysis. The processor controls elements of the configurable analog signal conditioning circuit, the multiplexor, and the analog-to-digital converter, as well as other components of the configurable vibration sensor. In some embodiments of the invention, such other components can include memory, a digital-to-analog converter, and/or a communications interface, for example. The control functions of the processor may be defined in software instructions that are executed by the processor.

In accordance with the present invention, a configurable analog signal conditioning circuit of a configurable vibration sensor comprises a variable bandwidth filter. The operation of the variable bandwidth filter is controlled by the processor. The output from the variable bandwidth filter based on a given input can be varied by the processor by adjusting an associated bandwidth setting. For example, in one embodiment of the invention, the variable bandwidth filter applies a desired low pass filter to the analog signal received as input to the variable bandwidth filter, with a turning point selected by the processor.

In one embodiment of the invention, a configurable analog signal conditioning circuit of a configurable vibration sensor also comprises a variable gain amplifier. The variable bandwidth filter and variable gain amplifier cooperate to generate an analog output of the configurable analog signal conditioning circuit that may be ultimately transmitted to the processor for further processing and analysis. The operation of the variable gain amplifier is also controlled by the processor. For example, the output from the variable gain amplifier based on a given input can be varied by the processor by adjusting an associated amplifier setting, to change the bias and/or gain of the analog signal received as input to the variable gain amplifier.

In one embodiment of the invention, bandwidth settings and/or amplifier settings for a configurable vibration sensor can be adjusted through the use of an external device such as a computer.

These and other features of embodiments of the invention will now be described in greater detail with reference to the Figures.

Referring to FIG. 1, a schematic diagram of a configurable vibration sensor in an embodiment of the invention is shown generally as 10. Configurable vibration sensor 10 comprises a number of components, provided within an enclosure 20. Enclosure 20 facilitates protection of the internal components from foreign objects and damage, as well as the mounting of configurable vibration sensor 10 to a machine or other structure [not shown] for which vibrations are to be measured.

Components that permit configurable vibration sensor 10 to be configured for different vibration measurement applications are provided in a single device, so that a single sensor can perform the functions of many different components that might otherwise be implemented using separate devices physically distributed on a particular machine.

Configurable vibration sensor 10 comprises one or more analog sensor circuits 30, each comprising a vibration sensing element 32 connected to configurable analog signal conditioning circuit 34. Vibration sensing element 32 is an inertial sensor, such as an analog accelerometer. Other examples of vibration sensing elements 32 that may be used include rate gyroscopes, magnetometers, proximeters, seismic-velocity pickups, force transducers, and microphones, for example. Where configurable vibration sensor 10 comprises multiple analog sensor circuits 30, different vibration sensing elements 32 may be used in different analog sensor circuits 30. In one typical implementation of this embodiment of the invention, either two or three analog accelerometers are provided in configurable vibration sensor 10, each in a corresponding analog sensor circuit 30, so that vibrations in two or three orthogonal Cartesian directions respectively can be measured.

Each configurable analog signal conditioning circuit 34 contains one or more configurable elements that operate on analog signals output from vibration sensing element 32. The configurable elements comprise a variable bandwidth filter 36 coupled to vibration sensing element 32. In one embodiment of the invention, variable bandwidth filter 36 applies a desired low pass filter to the analog signal it receives as input. Variable bandwidth filter 36 may be an integrated circuit that implements a Butterworth or elliptic filter, for example. In variant embodiments of the invention, other filters may be used, including high-pass filters or band-pass filters, for example.

The term "coupled" as used in the specification and in the claims is not restricted to meaning "directly coupled" or "directly connected", as it may also be used to describe a relationship in which elements or components are connected to each other through other elements or components.

In this embodiment of the invention, the configurable elements also comprise a variable gain amplifier 38 coupled to vibration sensing element 32. Variable gain amplifier 38 changes the bias and/or gain of the analog signal it receives as input. Variable gain amplifier 38 cooperates with variable bandwidth filter 36 to generate an analog output of configurable analog signal conditioning circuit 34 that can be transmitted to a processor 40 for further processing and analysis.

In a configurable analog signal conditioning circuit 34 shown in FIG. 1, variable bandwidth filter 36 is shown coupled to vibration sensing element 32 through variable gain amplifier 38. In operation, variable gain amplifier 38, being coupled between vibration sensing element 32 and variable bandwidth filter 36, receives as input the analog signal output from vibration sensing element 32, changes the bias and/or gain of the analog signal output from vibration sensing element 32, and produces as its output an analog signal. The output of variable gain amplifier 38 is then provided as input to variable bandwidth filter 36, which applies a desired low pass filter to the input to variable bandwidth filter 36 and produces as its output an analog signal. In this embodiment, the output of variable bandwidth filter 36 represents the output of configurable analog signal conditioning circuit 34 that can be transmitted to processor 40 for further processing and analysis.

In variant embodiments of the invention, configurable analog signal conditioning circuit 34 may contain configurable elements different from those described above and/or additional configurable elements. In variant embodiments of the invention, configurable analog signal conditioning circuit 34 may contain additional non-configurable elements. Where configurable vibration sensor 10 comprises multiple analog sensor circuits 30, different combinations of elements may be employed in different analog sensor circuits 30.

Furthermore, in variant embodiments of the invention, the arrangement of elements of configurable analog signal conditioning circuit 34 may also be different from the arrangement described above. For example, the positions of variable bandwidth filter 36 and variable gain amplifier 38 may be switched, so that variable bandwidth filter 36 is coupled between vibration sensing element 32 and variable gain amplifier 38. In operation, variable bandwidth filter 36 operates on the analog signal output from vibration sensing element 32 to produce output, which in turn is provided to variable gain amplifier 38. Variable gain amplifier 38 changes the bias and/or gain of the analog signal output from variable bandwidth filter 36 and produces as output an analog signal, which represents the output of configurable analog signal conditioning circuit 34 that can be transmitted to processor 40 for further processing and analysis. Other arrangements are possible depending on the composition of configurable analog signal conditioning circuit 34.

Processor 40 is coupled to and controls the operation of the configurable elements of configurable analog signal conditioning circuit 34, to vary the output of configurable analog signal conditioning circuit 34. Where the components of configurable vibration sensor 10 are implemented using integrated circuits, various components may be coupled to the input/output pins of processor 40 via circuit traces, for example.

Where there are multiple configurable elements, each element can be separately controlled by processor 40, through separate control signals from processor 40, for example. Furthermore, where configurable vibration sensor 10 comprises multiple analog sensor circuits 30, the configurable analog signal conditioning circuit 34 of each analog sensor circuit 30 can be controlled independently by the processor.

For example, the manner in which the operation of any one variable bandwidth filter 36 in configurable vibration sensor 10 can be varied is independent of how processor 40 may direct the operation of other variable bandwidth filters 36 to be varied. Similarly, the manner in which the operation of any one variable gain amplifier 38 in configurable vibration sensor 10 can be varied is independent of how processor 40 may direct the operation of other variable gain amplifiers 38 to be varied.

Processor 40 controls the operation of each variable bandwidth filter 36 by communicating the respective desired low pass filter to a respective variable bandwidth filter 36 using, for example, the Serial Peripheral Interface (SPI) serial communications protocol of the variable bandwidth filter 36. It will be understood by persons skilled in the art that the specific method for communicating with the variable bandwidth filter 36 will depend upon the specific components utilized in a particular implementation. The operation of the respective variable bandwidth filter 36 is varied by processor 40 based on one or more associated bandwidth settings. One example of a bandwidth setting is a turning point associated with the filter. Depending on the value of this bandwidth setting, processor 40 will apply the desired filter with the set turning point to the respective input signal. The currently set values of the bandwidth settings for the various variable bandwidth filters 36 are stored in a memory 42 coupled to processor 40.

Similarly, processor 40 controls the operation of each variable gain amplifier 38 by communicating the respective desired gain of the respective input signal and/or the respective desired offset of the respective input signal to the variable gain amplifier 38, to vary the output of the respective variable gain amplifier 38 using, for example, the SPI serial communications protocol of the variable gain amplifier 38. It will be understood by persons skilled in the art that the specific method for communicating with the variable gain amplifier 38 will depend upon the specific components utilized in a particular implementation. The operation of the respective variable gain amplifier 38 is varied by processor 40 based on one or more associated amplifier settings. Amplifier settings may include a bias setting and/or gain setting for example, as noted above. The currently set values of the amplifier settings for the various variable gain amplifiers 38 are also stored in memory 42.

Physically, memory 42 can be implemented using one or more known memory devices or components, including flash memory 44 and random access memory (RAM) 46 for example.

In one embodiment of the invention, a default set of values for bandwidth settings and/or amplifier settings may be stored in a non-volatile storage device, such as flash memory 44, for example. When processor 40 is initially powered up or reset, processor 40 may use these default values to initially configure the variable bandwidth filters 36 and variable gain amplifiers 38 of analog sensor circuits 30 to operate based on the respective set bandwidth settings and amplifier settings.

Memory 42 may also be used to store software instructions that are to be executed by the processor for controlling the configurable elements of configurable analog signal conditioning circuit 34. The instructions can be associated with one or more configuration algorithms. For example, in an embodiment of the invention, the configuration algorithms may include one or more bandwidth configuration algorithms. When the associated instructions are executed by processor 40, the value of one or more bandwidth settings may be adjusted (e.g. by setting or modifying the value(s) in memory 42) as determined by the bandwidth configuration algorithms. By adjusting selected bandwidth settings, the operation of selected variable bandwidth filters 36 can be varied by processor 40.

As a further example, in another embodiment of the invention, the configuration algorithms may also include one or more amplifier configuration algorithms. When the associated instructions are executed by processor 40, the value of one or more amplifier settings may be adjusted (e.g. by setting or modifying the value(s) in memory 42) as determined by the amplifier configuration algorithms. By adjusting selected amplifier settings, the operation of selected variable gain amplifiers 38 can be varied by processor 40.

In another embodiment of the invention, the bandwidth settings and/or amplifier settings stored in memory 42 (e.g. flash memory 44) can be changed by an external device, such as a computer. By changing the bandwidth settings and/or amplifier settings in memory 42, the operation of variable bandwidth filters 36 and variable gain amplifiers 38, which operate based on these respective settings, can be varied. In this manner, configurable vibration sensor 10 can thus be configured for different vibration measurement applications.

In one embodiment of the invention, configurable vibration sensor 10 also comprises a multiplexor 50, for use when more than one analog sensor circuit 30 is employed. Multiplexor 50 is controlled by processor 40, and is used to select output signals from specific analog sensor circuits 30 to be transmitted to processor 40, through an analog-to-digital converter 52, to provide the selected output signals from selected analog sensor circuits 30 to processor 40 in digital form.

In variant embodiments of the invention, multiple multiplexors 50 and/or analog-to-digital converters 52 may be employed. Other components may also be employed along the path from analog sensor circuits 30 to processor 40.

The digital signals received by processor 40 may then be analyzed by one or more digital filters that are stored in memory 42, and that can be applied by processor 40. Each digital filter can be customized for signals originating from different vibration sensing elements 32, by adjusting one or more filter configuration parameters associated with each digital filter. The filter configuration parameters are stored in memory 42 (e.g. flash memory 44). The digital filters may include, for example, configurable digital bandpass filters, root-mean-square (RMS) level calculators, peak-to-peak level calculators, and Fast Fourier Transforms.

Configurable alarm logic or event logic may also be available. The alarm logic can be configured to save data derived from the output of specific analog sensor circuits 30 of interest at a particular time in memory 42. The data may include one or more digital signals and a time record, for example. The time series sensor data may be saved in memory 42 for a certain period of time, to be later retrieved by an external device through a communications interface to analyze the events detected and captured by the alarm.

One example of a communications interface may be a digital-to-analog converter 60, through which data may be transmitted to an external device adapted to receive analog input [not shown]. One example of such a device is a machine safety shutdown circuit that is triggered by the alarm generated by configurable vibration sensor 10.

Another example of a communications interface may be a digital communications interface 62, through which data may be transmitted to an external device adapted to receive digital input, such as a computer 70.

In one embodiment of the invention, data can also be transmitted from the external device (e.g. computer 70) to processor 40 of configurable vibration sensor 10. In operation, the external device can direct processor 40 to modify the values of one or more bandwidth settings and/or one or more amplifier settings stored in memory 42, thereby changing the configuration of configurable vibration sensor 10. The operation of one or more variable bandwidth filters 36 and/or one or more variable gain amplifiers 38 can therefore be varied, as these elements operate based on their associated bandwidth and amplifier settings respectively, as stored in memory 42.

In variant embodiments of the invention, filter configuration parameters stored in memory 42 may also be modified at the direction of an external device.

The communications interfaces can include both wired and wireless communications mechanisms. Some examples of communications interfaces that may be employed include RS-232, RS-482/485, IEEE 1394, Bluetooth®, Universal Serial Bus, and infrared serial communications.

With respect to the transmission of data by processor 40 to an external device, it will be understood by persons skilled in the art that such data need not be stored in memory 42 before it is transmitted to an external device. For example, a processor may directly transmit data to an external device through an appropriate communications interface without first storing the data in memory 42. However, in one embodiment of the invention, the storing of sensor data derived from the output of specific analog sensor circuits 30 in memory 42 memory is automatic, according to a method that respects the limited resources available with respect to both memory and processor resources. In accordance with this method, processor 40 stores all such sensor data in a cache within memory 42 (e.g. in RAM 46), so that a configurable period of the most recently acquired sensor data is always available. Multiple caches may also be established in memory 42, if desired. In this way, if a particular cache contains data that triggered an alarm condition (e.g. based on the alarm logic), that cache could act as a temporary buffer for the data until it is further analyzed. In the meantime, a new cache can be established to continue storing recently acquired sensor data.

Processor 40 can be implemented as either a Digital Signal Processor (e.g. Texas Instruments' TMS320C2000 Digital Signal Processors) or a microcontroller (e.g. Texas Instruments MSP430 microcontrollers), for example. Components such as memory 42, multiplexor 50, analog-to-digital converter 52, and communications interfaces such as digital-to-analog converter 60 and digital communications interface 62, where employed in a given implementation of configurable vibration sensor 10, may be provided as separate components or as peripherals of processor 40. It will be understood by persons skilled in the art that processor 40 may execute other control programs directed to the general operation thereof.

It will be understood by persons skilled in the art that a number of components of configurable vibration sensor 10 will require power to operate. The requisite power may be provided by way of an internal power source within enclosure 20, such as a battery in one embodiment of the invention [power source and connections not shown]. In another embodiment of the invention, configurable vibration sensor 10 may include a power regulator or power regulation circuit 80, which can be used to draw power from an external power source for supply to one or more components of configurable vibration sensor 10 [connections to components not shown]. Power regulator 80 can be supplied by power from a shared communication medium [not shown in FIG. 1] coupled to digital communications interface 62, or from a separate power supply [not shown in FIG. 1]. Different examples of means for powering components of configurable vibration sensor 10 will be described in greater detail with reference to FIG. 3a through FIG. 3d.

In one embodiment of the invention, components of configurable vibration sensor 10 are enclosed within enclosure 20 such that only digital communications interface 62 and power regulator 80 can be accessed externally. Where implemented, enclosure 20 may also provide access to the output of digital-to-analog converter 60. For example, enclosure 20 can encompass the components with a hermetic seal through which only power and digital communications with the components by external devices are capable. Reducing the number of external ties through enclosure 20 is beneficial both in terms of usability and reliability, since fewer access points to the internal elements of configurable vibration sensor 10 can decrease the likelihood that hazardous material from the external environment may interfere with the operation of configurable vibration sensor 10.

Figure 2A:
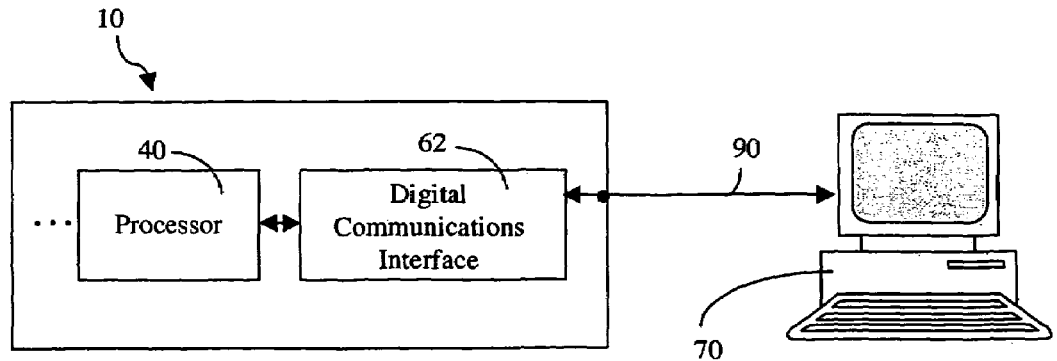
FIG. 2a is a schematic diagram illustrating an example configuration of a system in which a personal computer is coupled to a configurable vibration sensor in an embodiment of the invention.

Referring to FIG. 2a, a schematic diagram illustrating an example configuration of a system in which a personal computer is coupled to a configurable vibration sensor in an embodiment of the invention is shown. In this embodiment, configurable vibration sensor 10 communicates with personal computer 70 through digital communications interface 62 coupled directly to personal computer 70 via a direct connection 90. The direct connection 90 need not be a physical connection, but may be wireless or comprise a combination of wired and wireless components. Although configurable vibration sensor 10 comprises a number of components (e.g. as shown in the embodiment illustrated in FIG. 1), only a subset of those components have been shown in the example of FIG. 2a.

Figure 2B:
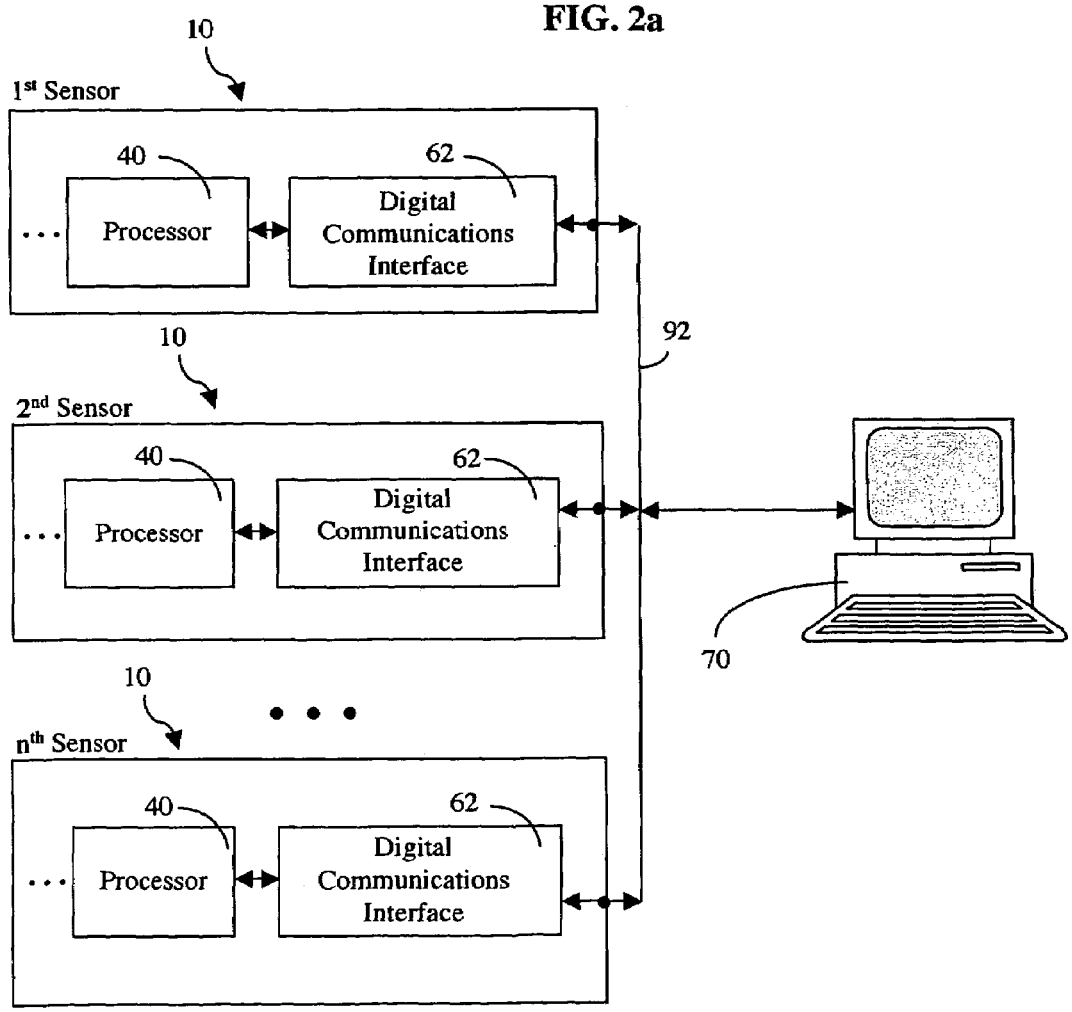
FIG. 2b is a schematic diagram illustrating an example configuration of a system in which a personal computer is coupled to multiple configurable vibration sensors in an embodiment of the invention.

Referring to FIG. 2b, a schematic diagram illustrating an example configuration of a system in which a personal computer is coupled to multiple configurable vibration sensors in an embodiment of the invention is shown. In this embodiment, each of a plurality of configurable vibration sensors 10 can communicates with personal computer 70 through its respective digital communication interface 62 coupled to personal computer 70 through a bus connection 92. Connections to the bus or personal computer 70 need not be a physical connection, but may be wireless or comprise a combination of wired and wireless components. Although each configurable vibration sensor 10 comprises a number of components (e.g. as shown in the embodiment illustrated in FIG. 1), only a subset of those components have been shown in the example of FIG. 2b.

In one embodiment of the invention, each configurable vibration sensor 10 has an identifier stored in memory (e.g. flash memory 46 of FIG. 1) that uniquely identifies that configurable vibration sensor 10 to computer 70. Computer 70 can act as a bus master. Master computer 70 can collect the data from each configurable vibration sensor 10 coupled to connection 92, either in real-time, or by transferring data stored in its respective memory (e.g. 42 of FIG. 1), including data that may be stored in a cache. Individual configurable vibration sensors 10 will return the contents of their respective caches to master computer 70 to reduce the communications overhead. By transmitting a cache of samples instead of individual samples, the total data transmitted will typically be reduced since there is also data associated with the overhead communications protocol that would be replicated every time the monitoring of communications is switched from one configurable vibration sensor 10 to another.

In some scenarios where many configurable vibration sensors 10 share a common bus, it may not be possible for all of them to send back data to master computer 70 in real time or pseudo real time. In these situations, configurable vibration sensors 10 in one embodiment of the invention are also capable of receiving an initiation signal, at which point all configurable vibration sensors 10 will cache data for a fixed interval. In this manner, each configurable vibration sensor 10 is individually sampling vibrations at a specific time separately, but without a time phase difference between samples on separate configurable vibration sensors 10. When the interval has expired, the data from all configurable vibration sensors 10 can be collected individually, to generate a dataset where the separately sampled data is coordinated.

Configurable vibration sensors 10 on the bus can also be configured as a group under the direction of master computer 70. In this operation, each configurable vibration sensor 10 has an additional address identifier that is not unique on the bus and is recognized by the configurable vibration sensor 10 as a universal bus address that it will also respond to in addition to its unique identifier. This method is typically only possible in bus implementations that allow bus devices (i.e. configurable vibration sensors 10) to respond to multiple addresses.

Configurable vibration sensor 10 can be powered in various configurations, as will now be described in greater detail with reference to the examples of FIG. 3a through FIG. 3d. Although configurable vibration sensor 10 comprises a number of components (e.g. as shown in the embodiment illustrated in FIG. 1), only a subset of those components have been shown in the examples of FIG. 3a through FIG. 3d. These figures also illustrate different example configurations in which configurable vibration sensor 10 can be coupled to various external devices. In use, configurable vibration sensor 10 may switch between these and other configurations.

Figure 3A:
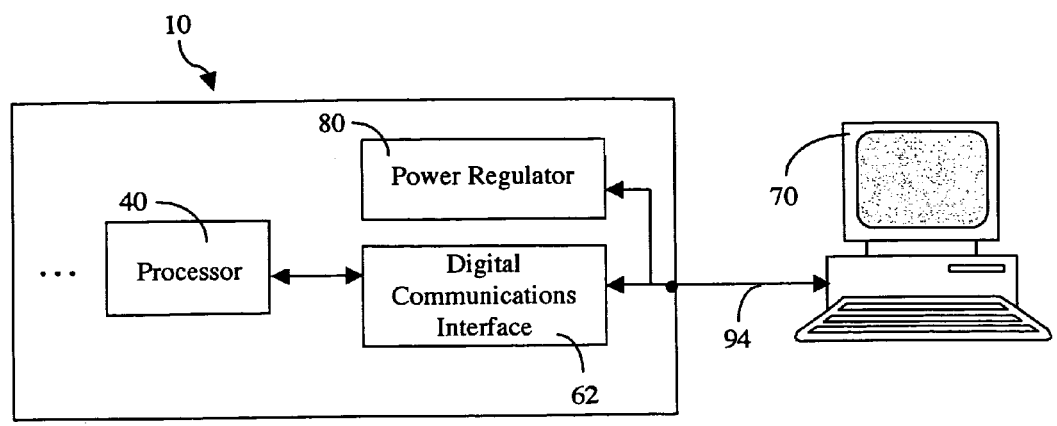
FIG. 3a is a schematic diagram illustrating an example configuration of a system in which power is received from a shared communication medium through a power regulator of a configurable vibration sensor in an embodiment of the invention.

Referring to FIG. 3a, a schematic diagram illustrating an example configuration of a system in which power is received from a shared communication medium through a power regulator of a configurable vibration sensor in an embodiment of the invention is shown. In this embodiment, power regulator 80 and digital communications interface 62 are coupled to a shared communications medium 94 adapted to transmit both power and communications between configurable vibration sensor 10 and personal computer 70. Shared communications medium 94 may be a Universal Serial Bus, IEEE-1394, or other medium that facilitates transmission of both power and communications.

Figure 3B:
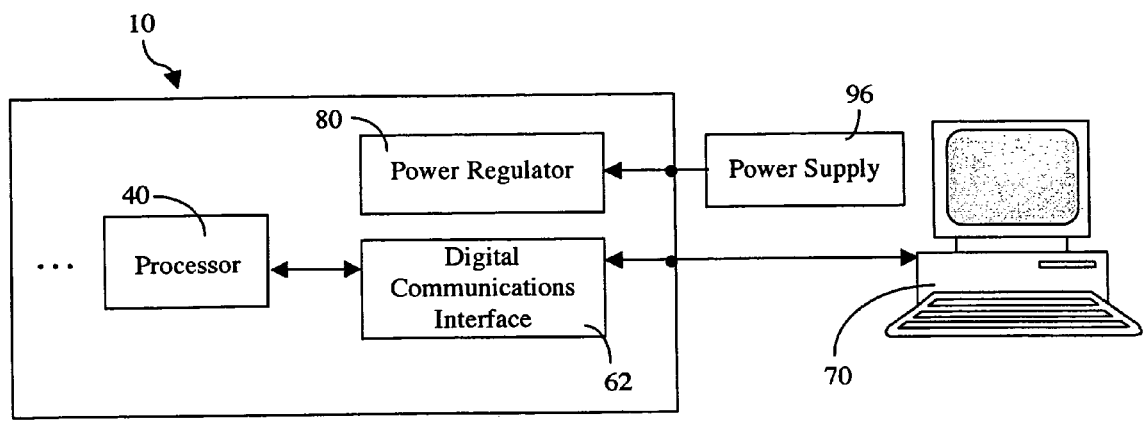
FIG. 3b is a schematic diagram illustrating an example configuration of a system in which power is received from a power supply through a power regulator of a configurable vibration sensor in an embodiment of the invention.

Referring to FIG. 3b, a schematic diagram illustrating an example configuration of a system in which power is received from a power supply through a power regulator of a configurable vibration sensor in an embodiment of the invention is shown. In this embodiment, power regulator 80 is coupled to a power supply 96 that is separate from digital communications interface 62. Power supply 96 could either be portable (e.g. battery) or powered from a wired source such as electric mains. Digital communications interface 62 is coupled to personal computer 70 through a separate connection.

FIG. 3a and FIG. 3b illustrate configurations in which computer 70 is coupled to configurable vibration sensor 10 in a way that permits computer 70 to transmit information to and control the configurable elements of the configurable vibration sensor 10.

Figure 3C:
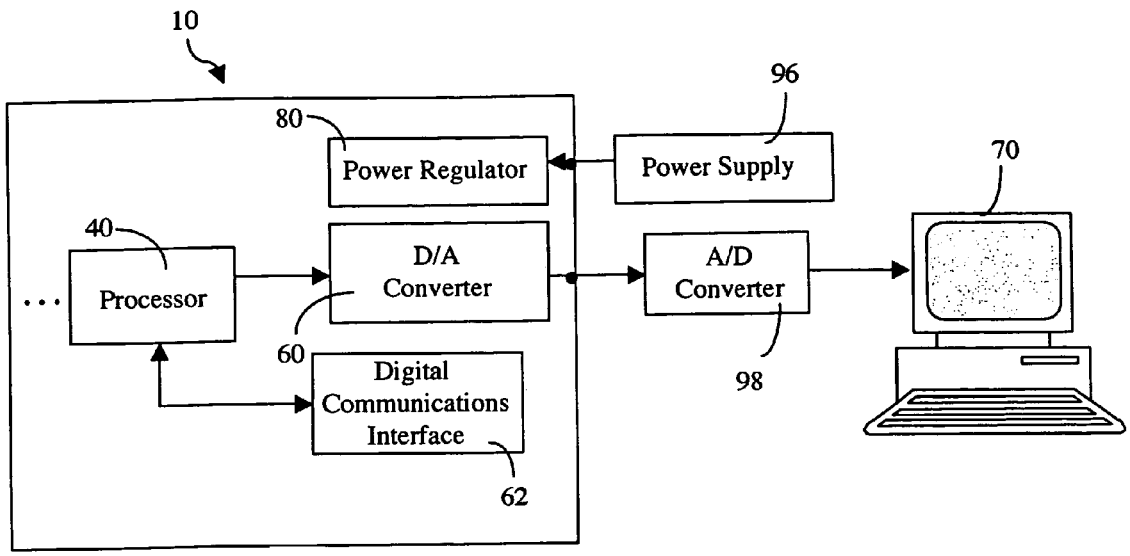
FIG. 3c is a schematic diagram illustrating another example configuration of a system in which power is received from a power supply through a power regulator of a configurable vibration sensor in an embodiment of the invention.

Referring to FIG. 3c, a schematic diagram illustrating another example configuration of a system in which power is received from a power supply through a power regulator of a configurable vibration sensor in an embodiment of the invention is shown. In this embodiment, power regulator 80 is connected to power supply 96 that is separate from digital communications interface 62. Power supply 96 could either be portable (e.g. battery) or powered from a wired source such as electric mains. Digital communications interface 62 is not connected to personal computer 70; instead, digital-to-analog converter 60 is connected via an analog signal wire to an external analog-to-digital converter 98. Analog-to-digital converter 98 may either be a separate component, or it may be implemented as a peripheral card in personal computer 70. In this configuration, digital communications interface 62 is idle, and computer 70 cannot control the configurable elements of configurable vibration sensor 10.

Alternatively [not shown], digital-to-analog converter 60 can be connected to another device such as a controller that uses the analog signal as an input. The digital-to-analog converter is controlled by a program running on processor 40, which in one embodiment of the invention, can be uploaded to configurable vibration sensor 10 when previously attached to personal computer 70 (e.g. when the system was configured as shown in FIG. 3a or FIG. 3b).

Figure 3D:
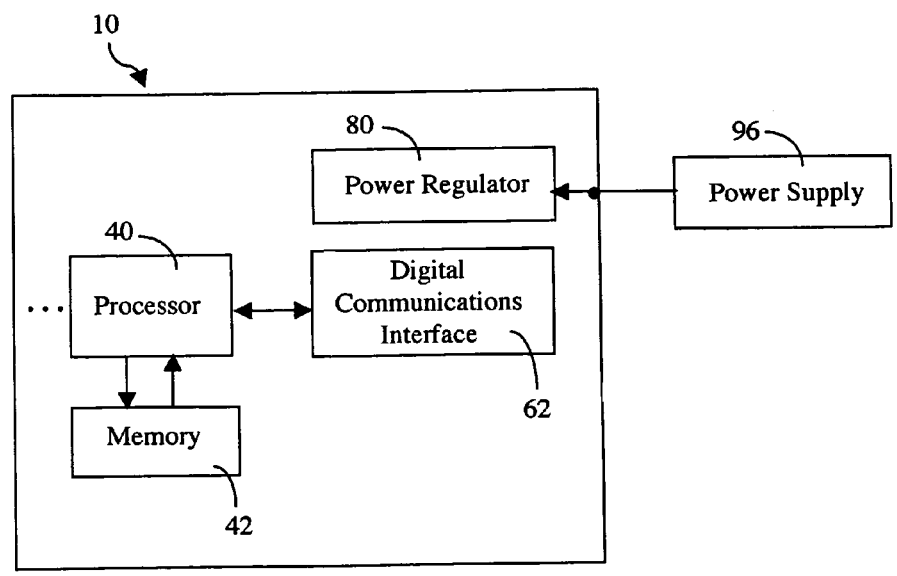
FIG. 3d is a schematic diagram illustrating another example configuration of a system in which power is received from a power supply through a power regulator of a configurable vibration sensor in an embodiment of the invention.

Referring to FIG. 3d, a schematic diagram illustrating another example configuration of a system in which power is received from a power supply through a power regulator of a configurable vibration sensor in an embodiment of the invention is shown. In this embodiment, power regulator 80 is connected to power supply 96 that is separate from digital communications interface 62. Neither the digital communications interface 62 nor the digital-to-analog converter [not shown in FIG. 3d] is connected to any external device in this configuration. A program being executed by processor 40 is caching information in memory 42. At a later period, cached data in memory 42 will be transmitted to a personal computer by connecting configurable vibration sensor 10 to a personal computer, in one of the configurations shown in FIGS. 3a–3c, for example. As in FIG. 3c, in this configuration, digital communications interface 62 is idle, and computer 70 cannot control the configurable elements of configurable vibration sensor 10.

Figure 4:
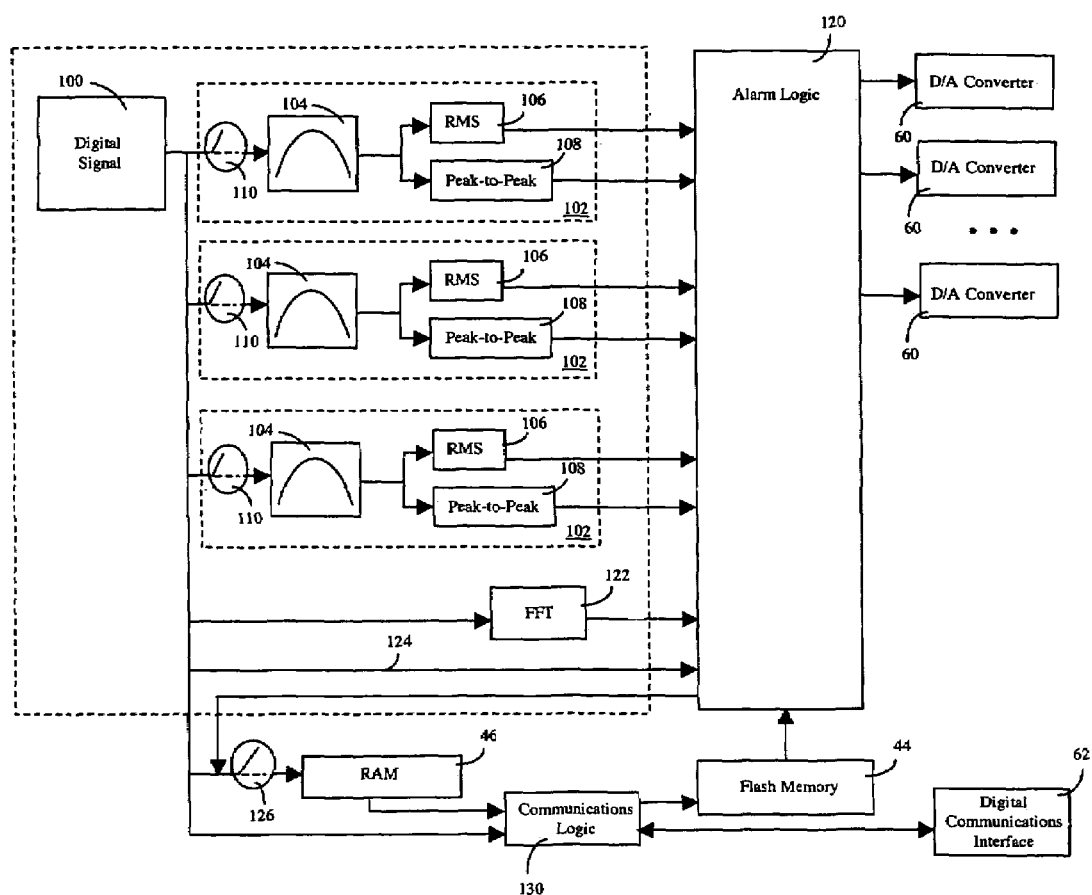
FIG. 4 is a schematic diagram illustrating a data flow of digital vibration signals through the processor of a configurable vibration sensor in an embodiment of the invention.

Referring to FIG. 4, a schematic diagram illustrating a data flow of digital vibration signals through the processor of a configurable vibration sensor in an embodiment of the invention is shown. The digital signal and filter components of FIG. 4 are shown conceptually; this Figure primarily illustrates that the alarm logic employed in this embodiment of the invention is a function of multiple digital filters that can be separately configured.

A digital signal 100 derived from an analog sensor circuit (e.g. 30 of FIG. 1) can be processed by a processor (e.g. 40 of FIG. 1) of a configurable vibration sensor (e.g. 10 of FIG. 1) by applying any of a number of configurable digital filters 102 to digital signal 100. In the example implementation shown, each configurable digital filter 102 consists of a configurable bandpass filter 104, RMS level measurements 106 and Peak-to-Peak level measurements 108 that are configured, based upon values stored in memory (e.g. flash memory 44 of FIG. 1). Any particular configurable digital filter 102 may or may not be applied to digital signal 100 as directed by the processor, as shown conceptually by switches 110. When a particular configurable digital filter 102 is applied to digital signal 100, a filtered signal is produced as output from the respective digital filter and made available to a program implementing the alarm logic 120. Digital signal 100 may also be passed to alarm logic 120 after undergoing a Fast Fourier Transformation at 122, or directly to alarm logic 120 at 124.

Data received by alarm logic 120 may also be cached in RAM 46 as controlled by the processor as shown conceptually by switch 126. The digital signal can also be stored directly in RAM 46 for later retrieval from the configurable vibration sensor. Data received by alarm logic 120 may also be transmitted to an external device through one or more digital-to-analog converters 60. The digital-to-analog converters 60 can produce any product of the alarm logic 120 including, for example, a step function to drive an external alarm device, or a signal corresponding to the confidence level of the alarm logic 120 that can drive a gauge for visual observation.

Communications logic 130 is employed when the configurable vibration sensor is connected to a personal computer [not shown in FIG. 4] through a digital communications interface 62. Communications logic 130 facilitates the storage of configuration values in flash memory 44 provided by the personal computer. The configuration values may be used by the processor to configure alarm logic 120. For example, the alarm logic could be reconfigured if the machine characteristics have changed, or if there is a particular condition that a user may want to monitor the occurrence of which has not been currently selected as an alarm condition.

Digital vibration data 100 may also be transmitted either in real-time or from a cache in RAM 46 to the personal computer through communications logic circuit 130 and communications interface 62.

The present invention has been described with reference to various embodiments. However, it will be understood by persons skilled in the art that a number of other variations or modifications are possible without departing from the scope of the invention as defined in the appended claims.

The invention claimed is:

1. A configurable vibration sensor comprising:
one or more sensor circuits;
one or more analog-to-digital converters coupled to the one or more sensor circuits, for converting output from the one or more sensor circuits to one or more digital signals;
a processor coupled to the one or more analog-to-digital converters, for processing the one or more digital signals;
a digital communications interface coupled to the processor, for facilitating the communication of at least data between the processor and a computer adapted to receive digital input; and
a power regulator, wherein the digital communications interface and the power regulator are coupled to the computer through a shared communications medium adapted to transmit power and data, and wherein in operation, the power regulator receives power through the shared communications medium for supply to one or more components of the configurable vibration sensor;
wherein each of the one or more sensor circuits comprises a vibration sensing element and a variable bandwidth filter coupled thereto; and
wherein each variable bandwidth filter of the one or more sensor circuits is controllable by the processor such that the operation of each variable bandwidth filter is variable by the processor.

2. The configurable vibration sensor of claim 1, wherein the operation of the variable bandwidth filter of each sensor circuit is independently variable by the processor.

3. The configurable vibration sensor of claim 1, further comprising memory coupled to the processor for storing bandwidth settings, wherein each variable bandwidth filter of the one or more sensor circuits is associated with one or more bandwidth settings; wherein in operation, the processor varies the operation of each variable bandwidth filter based on the value of the bandwidth setting associated therewith.

4. The configurable vibration sensor of claim 3, further comprising memory for storing instructions associated with one or more bandwidth configuration algorithms; wherein in operation, the instructions are executed by the processor such that the value of one or more bandwidth settings are adjustable as determined by the bandwidth configuration algorithms.

5. The configurable vibration sensor of claim 3, wherein the configurable vibration sensor is adapted for coupling to the computer such that the value of one or more bandwidth settings are adjustable by the computer.

6. The configurable vibration sensor of claim 1, wherein each of the one or more sensor circuits further comprises a variable gain amplifier coupled to the respective vibration sensing element thereof, and wherein each variable gain amplifier of the one or more sensor circuits is controllable by the processor such that the operation of each variable gain amplifier is variable by the processor.

7. The configurable vibration sensor of claim 6, wherein the operation of the variable gain amplifier of each sensor circuit is independently variable by the processor.

8. The configurable vibration sensor of claim 6, further comprising memory coupled to the processor for storing amplifier settings, wherein each variable gain amplifier of the one or more sensor circuits is associated with one or more amplifier settings; wherein in operation, the processor varies the operation of each variable gain amplifier based on the value of the amplifier setting associated therewith.

9. The configurable vibration sensor of claim 8, further comprising memory for storing instructions associated with one or more amplifier configuration algorithms; wherein in operation, the instructions are executed by the processor such that the value of one or more amplifier settings are adjustable as determined by the amplifier configuration algorithms.

10. The configurable vibration sensor of claim 8, wherein the configurable vibration sensor is adapted for coupling to the computer such that the value of one or more amplifier settings are adjustable by the computer.

11. The configurable vibration sensor of claim 1, further comprising a multiplexor coupled between the one or more sensor circuits and the processor, for providing the processor with output from at least one of the one or more sensor circuits.

12. The configurable vibration sensor of claim 11, wherein the multiplexor is controllable by the processor such that, in operation, the multiplexor provides output from at least one of the one or more sensor circuits as selected by the processor.

13. The configurable vibration sensor of claim 1, further comprising memory coupled to the processor for storing output generated by the processor, when the output generated by the processor is to be stored for later communication to the computer.

14. The configurable vibration sensor of claim 13, wherein the output generated by the processor for storing in memory comprises at least one of the one or more digital signals.

15. The configurable vibration sensor of claim 1, further comprising memory coupled to the processor for storing one or more digital filter programs and associated filter configuration parameters; wherein in operation, the processor executes selected digital filter programs such that one or more digital filters are applied to at least a subset of the one or more digital signals based on the configuration parameters associated with the applied digital filters.

16. The configurable vibration sensor of claim 15, wherein the configurable vibration sensor is adapted for coupling to the computer such that one or more filter configuration parameters are adjustable by the computer.

17. The configurable vibration sensor of claim 1, further comprising an enclosure, wherein the one or more sensor circuits, the one or more analog-to-digital converters, and the processor are provided within the enclosure.

18. The configurable vibration sensor of claim 17, wherein the enclosure permits the configurable vibration sensor to be coupled to the computer only through at least one of the digital communications interface and the power regulator.

19. A configurable vibration sensor comprising:
one or more sensor circuits;
one or more analog-to-digital converters coupled to the one or more sensor circuits, for converting output from the one or more sensor circuits to one or more digital signals;

a processor coupled to the one or more analog-to-digital converters, for processing the one or more digital signals;

an enclosure, wherein the one or more sensor circuits, the one or more analog-to-digital converters, and the processor are provided within the enclosure;

an external communications interface coupled to the processor; and a power regulator coupled to the processor;

wherein the enclosure permits the configurable vibration sensor to be coupled to an external device only through at least one of the external communications interface and the power regulator;

wherein each of the one or more sensor circuits comprises a vibration sensing element and a variable bandwidth filter coupled thereto; and wherein each variable bandwidth filter of the one or more sensor circuits is controllable by the processor such that the operation of each variable bandwidth filter is variable by the processor.

20. The configurable vibration sensor of claim 19, wherein the external communications interface comprises at least one of: a digital communications interface, and a digital-to-analog converter.

21. The configurable vibration sensor of claim 19, wherein the operation of the variable bandwidth filter of each sensor circuit is independently variable by the processor.

22. The configurable vibration sensor of claim 19, further comprising memory coupled to the processor for storing bandwidth settings, wherein each variable bandwidth filter of the one or more sensor circuits is associated with one or more bandwidth settings; wherein in operation, the processor varies the operation of each variable bandwidth filter based on the value of the bandwidth setting associated therewith.

23. The configurable vibration sensor of claim 22, further comprising memory for storing instructions associated with one or more bandwidth configuration algorithms; wherein in operation, the instructions are executed by the processor such that the value of one or more bandwidth settings are adjustable as determined by the bandwidth configuration algorithms.

24. The configurable vibration sensor of claim 22, wherein the configurable vibration sensor is adapted for coupling to the external device such that the value of one or more bandwidth settings are adjustable by the external device.

25. The configurable vibration sensor of claim 19, wherein each of the one or more sensor circuits further comprises a variable gain amplifier coupled to the respective vibration sensing element thereof, and wherein each variable gain amplifier of the one or more sensor circuits is controllable by the processor such that the operation of each variable gain amplifier is variable by the processor.

26. The configurable vibration sensor of claim 25, wherein the operation of the variable gain amplifier of each sensor circuit is independently variable by the processor.

27. The configurable vibration sensor of claim 25, further comprising memory coupled to the processor for storing amplifier settings, wherein each variable gain amplifier of the one or more sensor circuits is associated with one or more amplifier settings; wherein in operation, the processor varies the operation of each variable gain amplifier based on the value of the amplifier setting associated therewith.

28. The configurable vibration sensor of claim 27, further comprising memory for storing instructions associated with one or more amplifier configuration algorithms; wherein in operation, the instructions are executed by the processor such that the value of one or more amplifier settings are adjustable as determined by the amplifier configuration algorithms.

29. The configurable vibration sensor of claim 28, wherein the configurable vibration sensor is adapted for coupling to the external device such that the value of one or more amplifier settings are adjustable by the external device.

30. The configurable vibration sensor of claim 19, further comprising a multiplexor coupled between the one or more sensor circuits and the processor, for providing the processor with output from at least one of the one or more sensor circuits.

31. The configurable vibration sensor of claim 30, wherein the multiplexor is controllable by the processor such that, in operation, the multiplexor provides output from at least one of the one or more sensor circuits as selected by the processor.

32. The configurable vibration sensor of claim 19, wherein the external communications interface comprises a digital-to-analog converter coupled to the processor for converting output generated by the processor into analog form, to facilitate communication of output generated by the processor to the external device, the external device being adapted to receive analog input.

33. The configurable vibration sensor of claim 32, further comprising memory coupled to the processor for storing output generated by the processor prior to conversion into analog form, when the output generated by the processor is to be stored for later conversion into analog form and communication to the external device.

34. The configurable vibration sensor of claim 32, wherein the output generated by the processor for storing in memory comprises at least one of the one or more digital signals.

35. The configurable vibration sensor of claim 19, wherein the external communications interface comprises a digital communications interface coupled to the processor, for facilitating the communication of at least data between the processor and the external device, the external device being adapted to receive digital input.

36. The configurable vibration sensor of claim 35, further comprising memory coupled to the processor for storing output generated by the processor, when the output generated by the processor is to be stored for later communication to the external device.

37. The configurable vibration sensor of claim 35, wherein the output generated by the processor for storing in memory comprises at least one of the one or more digital signals.

38. The configurable vibration sensor of claim 19, further comprising memory coupled to the processor for storing one or more digital filter programs and associated filter configuration parameters; wherein in operation, the processor executes selected digital filter programs such that one or more digital filters are applied to at least a subset of the one or more digital signals based on the configuration parameters associated with the applied digital filters.

39. The configurable vibration sensor of claim 38, wherein the configurable vibration sensor is adapted for coupling to the external device such that one or more filter configuration parameters are adjustable by the external device.

40. A system comprising a plurality of configurable vibration sensors, wherein at least one of the plurality of configurable vibration sensors comprises one or more sensor circuits, one or more analog-to-digital converters coupled to the one or more sensor circuits for converting output from the one or more sensor circuits to one or more digital signals, and a processor coupled to the one or more analog-to-digital converters for processing the one or more digital signals, wherein each of the one or more sensor circuits comprises a vibration sensing element and a variable bandwidth filter coupled thereto, and wherein each variable bandwidth filter of the one or more sensor circuits is controllable by the processor such that the operation of each variable bandwidth filter is variable by the processor; and wherein the plurality of configurable vibration sensors are coupled to a computer through a bus connection.

* * * * *